United States Patent
Petit et al.

(10) Patent No.: US 6,915,715 B2
(45) Date of Patent: Jul. 12, 2005

(54) INSPECTION PROBE FOR AN INTERNAL WALL OF A DUCT

(75) Inventors: Michel Petit, Chatenoy le Royal (FR); Olivier Burat, Givry (FR)

(73) Assignee: Framatome ANP, Coubevoie (FR)

( * ) Notice: Subject to any disclaimer, the term of this patent is extended or adjusted under 35 U.S.C. 154(b) by 92 days.

(21) Appl. No.: 10/637,646

(22) Filed: Aug. 11, 2003

(65) Prior Publication Data

US 2004/0093966 A1 May 20, 2004

(30) Foreign Application Priority Data

Nov. 20, 2002 (FR) ............................................ 02 14542

(51) Int. Cl.⁷ .......................... G01D 21/00; G01H 11/00
(52) U.S. Cl. ...................................... 73/866.5; 73/661
(58) Field of Search ............................ 73/152.17, 598, 73/600, 622, 649, 661, 866.5

(56) References Cited

U.S. PATENT DOCUMENTS

| 4,981,044 | A |   | 1/1991 | Adams et al. |
| 5,503,019 | A |   | 4/1996 | Dewasmes |
| 5,533,404 | A | * | 7/1996 | Wurst et al. .................. 73/756 |
| 5,591,912 | A | * | 1/1997 | Spisak et al. ................. 73/623 |
| 5,652,387 | A |   | 7/1997 | Dumont et al. |

FOREIGN PATENT DOCUMENTS

EP            0 806 660            11/1997

* cited by examiner

*Primary Examiner*—Charles Garber
(74) *Attorney, Agent, or Firm*—Connolly Bove Lodge & Hutz LLP

(57) ABSTRACT

The invention relates to an inspection probe for an internal wall of a duct, comprising at least one sensor mounted in a support adapted to be moved inside the duct while pressing said sensor flat against said internal wall. The support is formed by a shell which is molded onto the sensor and comprises a body provided with a window for positioning said sensor and means for attaching said sensor flat against the internal wall of the duct, said means being integrally molded with the body.

The invention has applications in the non-destructive testing of ducts in nuclear power plants.

17 Claims, 3 Drawing Sheets

INSPECTION PROBE FOR AN INTERNAL WALL OF A DUCT

BACKGROUND OF THE INVENTION

The present invention relates to a non-destructive inspection probe for an internal wall of a duct, more particularly an internal wall of a duct in a nuclear power plant.

The invention likewise relates to a set of probes comprising multiple inspection probes.

In many industrial installations it is necessary to periodically carry out a check on the internal walls of ducts to verify that they are intact and in the interests of their operational reliability and safety. Operators are therefore obliged to perform increasing numbers of checks, for example on areas linking together the various elements and, should the need arise, to perform repairs of any faults that may have been detected.

This is, for example, the case with the internal walls in respect of passages in vessel floors in nuclear power plants of the pressurised water type.

The reason for this is that these passages in the vessel floor feature one end, projecting beneath the convex floor, joined to a non-rigid measurement duct allowing the floor of the vessel to communicate with a control room located within the fabric of the reactor building. Each of the ducts and the corresponding passage in the vessel floor can be negotiated with the finger of a glove in which a measurement probe is moved.

In order to enhance the operational reliability of nuclear reactors it is necessary to check the condition of the vessel floor cross-pieces to make sure that these pieces are still intact after the reactor has been operating for some time, particularly in the area where these cross-pieces are welded to the floor of the vessel.

This is also the case with the tubes of the steam generators with which nuclear reactors are fitted, which need to be examined on a regular basis.

To carry out these checks it is known to use probes, notably Foucault current probes and ultrasonic probes, which are moved along the internal wall of the duct under test.

The probes that have hitherto been used, and in particular ultrasonic probes, comprise at least one sensor mounted in a substantially cylindrical metal jacket made, for example, of aluminium or stainless steel, which has means for pressing said probe flat against the internal wall of the duct. These pressing means are constituted by a metallic spring that is generally positioned beneath the sensor or by a brush arrangement with soft bristles, usually disposed radially in order, first and foremost, to centre the probe in the duct.

Another type of probe is currently used to check an internal wall of an annular space such as a cover cross-piece for a nuclear reactor vessel fitted with a heat sleeve constituted by a coaxial internal duct.

However, these types of probes do not allow uniform contact between the sensor and the internal wall to be obtained while the sensor is being displaced within the duct, on account of the distortions and irregularities in the surface of said internal wall after the installation has been operating for some years.

In fact, the effectiveness of the test depends upon the effectiveness of the contact between the sensor and the internal wall of the area of duct under test, so much so that these contact defects manifest themselves as distortions in the test signals supplied by the probe.

It is the object of the present invention to propose an inspection probe that avoids these drawbacks by providing reliable, uniform contact between the sensor and the internal wall and that makes it possible to prolong the probe's useful life, while at the same time reducing manufacturing costs.

BRIEF SUMMARY OF THE INVENTION

The object of the invention is therefore an inspection probe for the internal wall of a duct, comprising at least one sensor mounted in a support that is adapted to be moved along the duct while pressing said sensor against the internal wall, characterised in that the support is formed by a shell moulded onto said sensor and comprising, on the one hand, a body equipped with a window for positioning said sensor and, on the other hand, means for pressing said sensor flat against the internal wall of the duct, said means being integrally moulded with the body.

According to further features of the invention:

- the duct presents a circular cross-section and the body has a substantially circular cross-section that is slightly smaller than that of said duct;
- the duct comprises an internal duct forming an annular space with said duct and the body has a substantially trapezoidal cross-section of a slightly lesser thickness then the width of said annular space;
- the pressing means include at least one body portion that is resilient and juts out with respect to said body, designed to bear against the internal wall of the duct or against an inner wall of the annular space so as to exert a force in the direction of the window and press the sensor flat against said internal wall;
- the pressing force which said resilient portion exerts on the sensor is between 2 and 25 newtons, preferably between 5 and 15 newtons;
- said resilient portion extends over at least part of the length of the body of the shell;
- said resilient portion extends the entire length of the body of the shell;
- said resilient portion is located on the body, opposite the sensor's contact generator with the internal wall;
- said resilient portion is located on the lateral edges of the body;
- said resilient portion is formed by two non-rigid pressing wings;
- the pressing wings are arranged 120° to either side of the sensor's contact generator with the internal wall;
- the shell is made from at least one polymer, for example polyurethane;
- the shell includes inserts, for example metal inserts;
- the sensor is an ultrasonic sensor.

A further object of the invention is a set of inspection probes, characterised in that it comprises multiple inter-articulated probes of the type already mentioned.

BRIEF DESCRIPTION OF THE SEVERAL VIEWS OF THE DRAWINGS

Further features and advantages of the invention will become apparent from the following description, which is given by way of example and refers to the accompanying drawings, wherein.

DETAILED DESCRIPTION OF THE INVENTION

Figure 1:
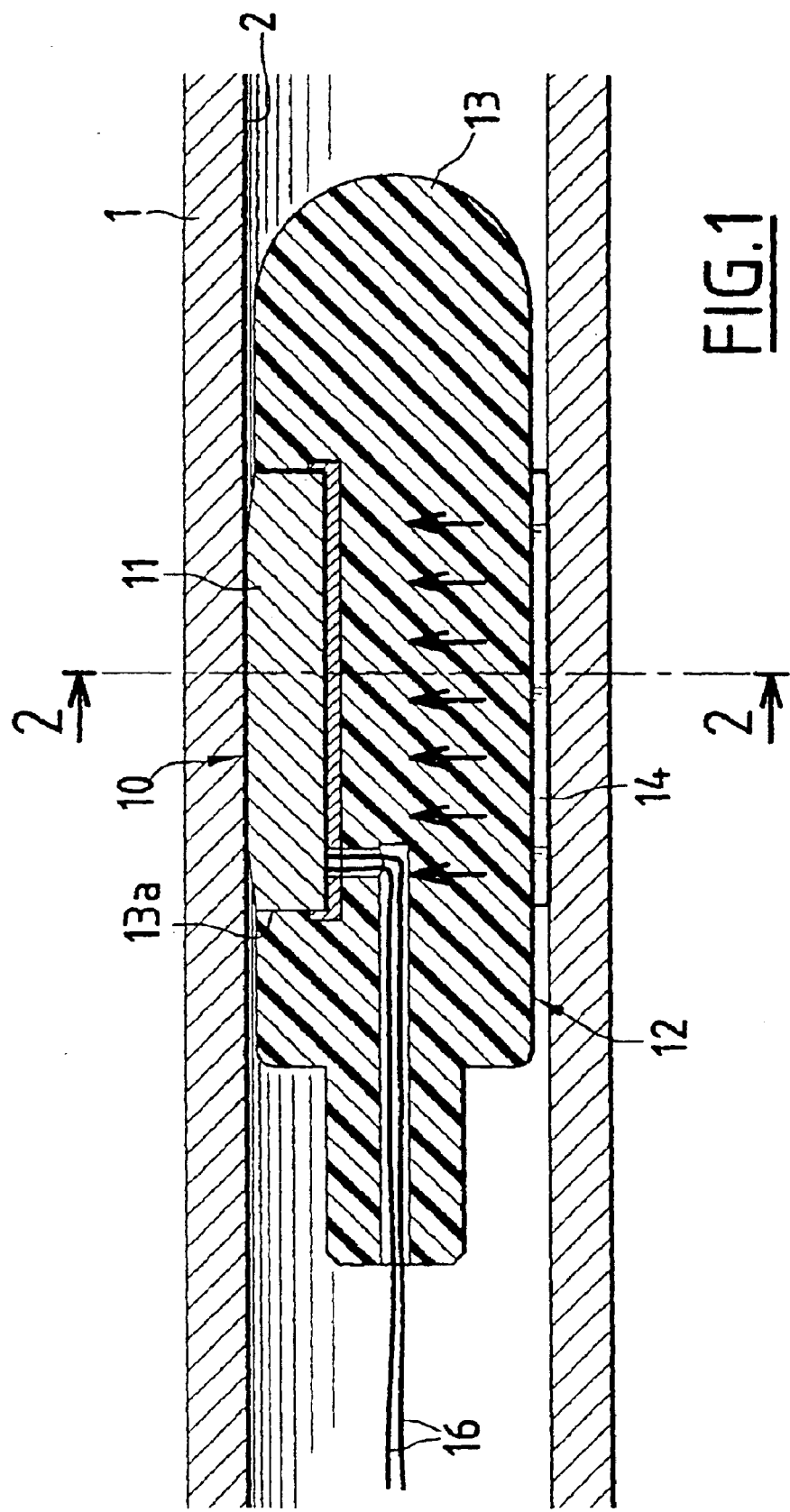
FIG. 1 shows a diagrammatic longitudinal section through an inspection probe according to the invention.

The inspection probe according to the invention, which is represented schematically in the Figures, is for example intended for ultrasonic testing of an internal wall 2 of a duct 1, for example internal walls of passages in the vessel floor in nuclear power plants of the pressurised water type.

The inspection probe, identified overall by reference number 10, is designed for introduction into the duct 1 and, in the embodiment represented in the Figures, includes a transceiver-type ultrasonic sensor 11.

According to one variant the probe 10 may have multiple sensors 11.

The sensor 11 is mounted in a support which is formed by a shell 12 moulded onto said sensor and having, on the one hand, a body 13 and, on the other, means 14 for pressing said sensor 11 flat against the internal wall of the duct 1.

Figure 2:
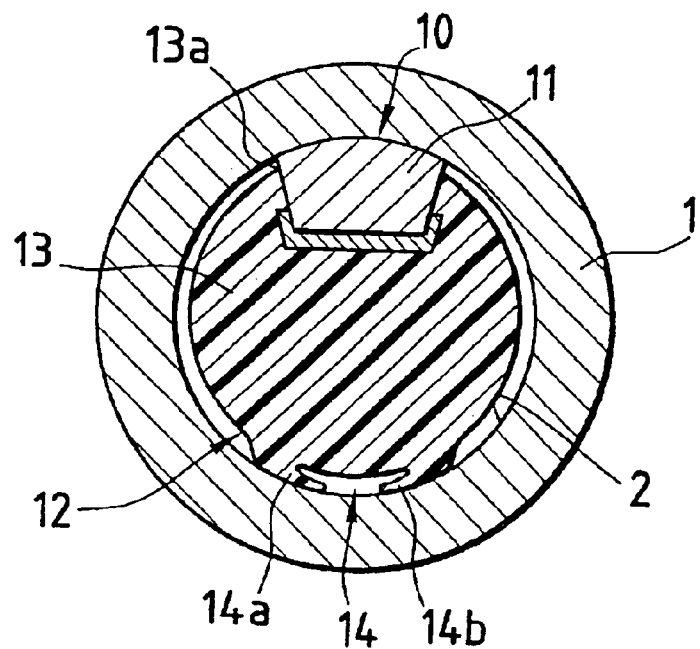
FIG. 2 shows a cross-section taken along line 2—2 in FIG. 1.
Figure 3:
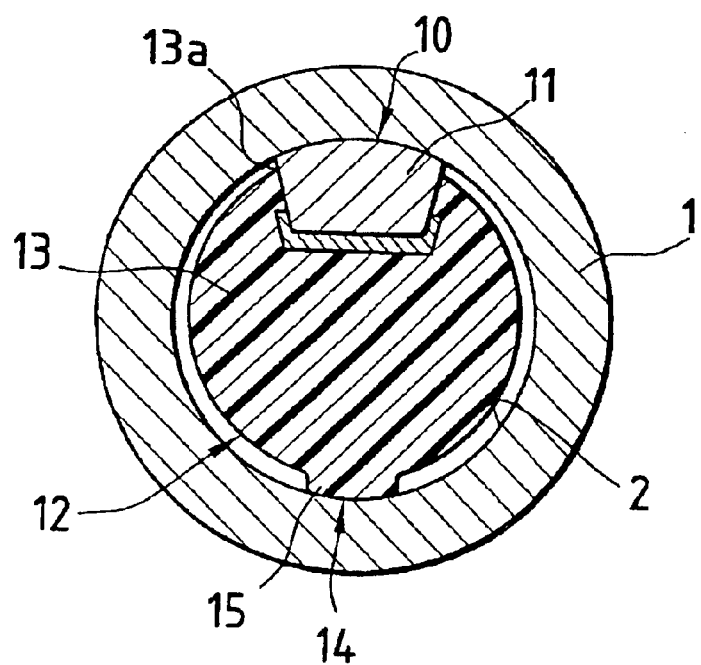
FIG. 3 shows a cross-sectional view of a variant of the inspection probe according to the invention.

According to a first embodiment depicted in FIGS. 1 to 3, the duct 1 presents a circular inner profile and the body 13 also presents a circular outer profile slightly smaller in section than the internal section of said duct 1. The body 13 presents a window 13a for positioning the sensor 11 in such a way that the external face of said sensor 11 juts out very slightly from the outer face of the body 13 of the shell 12.

In all cases the body 13 of the probe 10 presents an outer profile of complementary shape to the inner profile of the duct 1, but slightly smaller in section than the internal section of said duct 1.

As shown, especially in FIGS. 2 and 3, the pressing means 14 are integrally moulded with the body 13 and the shell 12 constituted by the body 13, and the pressing means 14 form a part consisting of a single piece.

Generally speaking, the pressing means feature at least one resilient portion 14 of the body 13, projecting with respect to said body, designed (as illustrated in the Figures) to rest against the internal wall 2 of the duct 1 so as to exert a force in the direction of the window 13a and press the sensor 11 flat against said internal wall 2.

It is preferred if the pressing force which the resilient portion 14 exerts on the sensor 11 is between 2 and 25 newtons, preferably between 5 and 15 newtons, and said resilient portion 14 is located on the body 13, in an arrangement diametrically opposite the contact generator for the sensor 11 with the internal wall 2.

The resilient portion 14 may extend over at least part of the length of the body 13, as depicted in FIG. 1, or it may extend the entire length of said body 13, or else it may be constituted by multiple portions distributed the length of said body 13.

According to one preferred form of embodiment depicted in FIG. 2, the resilient portion 14 is formed by two non-rigid wings, 14a and 14b respectively, which are integral with the body 13 and the free end of which bears against the internal wall 2 so as to each exert a pressing force the resultant of which is directed towards the window 13a of the body 13 so as to press the sensor 11 flat against the internal wall 2 of the duct 1. The wings 14a and 14b are arranged on either side of the contact generator of the sensor 11 with respect to the internal wall 2, preferably at an angle of 120°.

According to one variant represented in FIG. 3, the resilient portion 14 is constituted by at least one flange 15 which, when the shell 12 is introduced into the duct 1, becomes compressed and exerts a force directed at the window 13a of the body 13 so as to press the sensor 13 flat against the internal wall 2 of said duct 1.

The resilient portion 14 may take other forms and the chief condition to be fulfilled is that the difference between the internal section of the duct 1 and the external section of the body 13 must be decided so that the resilient portion 14 becomes compressed when the probe is introduced into the duct 1 and exerts a force on the sensor 11 that causes it to lie flat against the internal wall 2.

The sensor 11 is connected to a data processing unit by wires 16 which lead to the outside of the shell 12 and which can serve as a cable for pulling the probe 10 along inside the duct 2.

Figure 4:
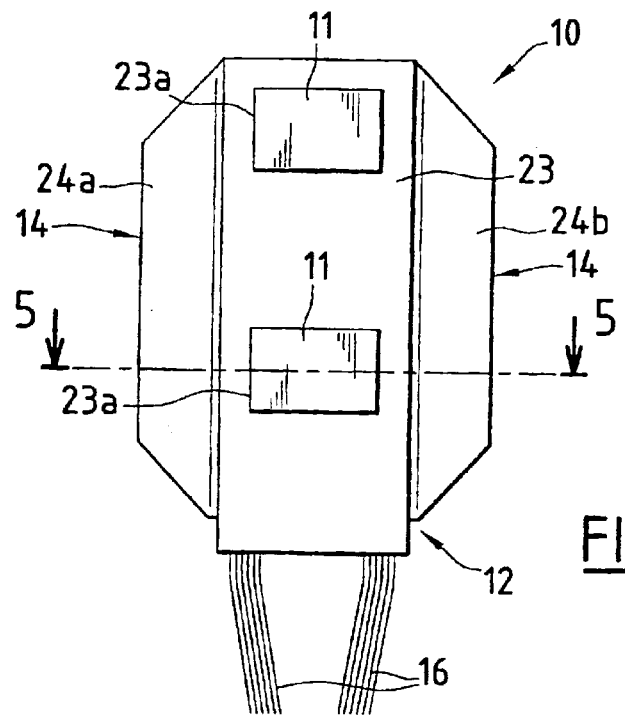
FIG. 4 shows a diagrammatic front view of a variant of an inspection probe according to the invention.
Figure 5:
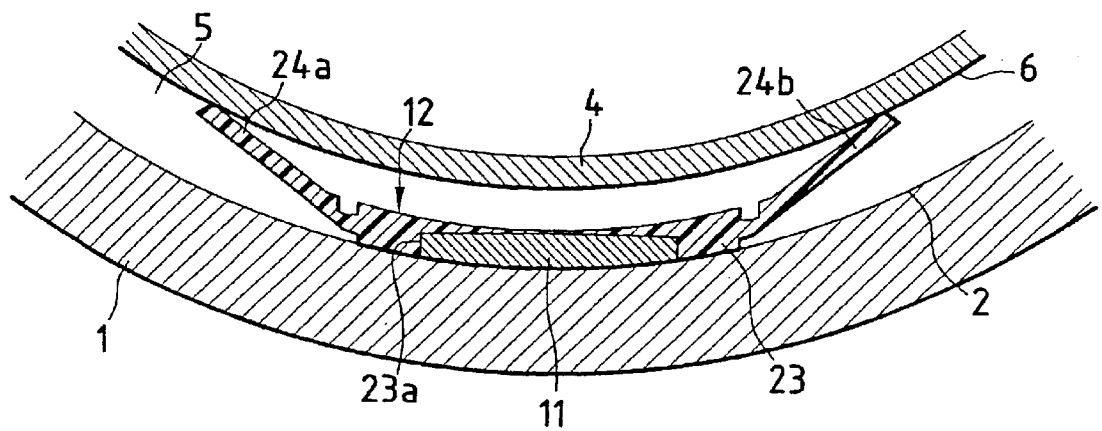
FIG. 5 shows a diagrammatic section taken along line 5—5 in FIG. 4.

FIGS. 4 and 5 depict an alternative use of the probe in accordance with the invention, which is to test an internal wall 2 of an annular space.

As FIG. 5 shows, the duct 1 features an internal duct 4 coaxial with said duct 1 and with the latter accommodating an annular space 5 delimited by the internal wall of the duct 1 and the external wall 6 of the duct 4.

In this case the shell 12 comprises a body 23 having a substantially trapezoidal cross-section of a slightly lesser thickness than the width of the annular space 5. The body 23 also presents a window 23a for positioning the sensor 11, and in the exemplary embodiment depicted in FIGS. 4 and 5 two windows 23a for positioning two sensors 11.

The pressing means 14 are likewise integrally moulded with the body 23 and are formed by two non-rigid wings 24a and 24b located on the lateral edges of said body 23. These wings 24a and 24b may extend over part or the full length of the body 23.

To carry out the test on the internal wall 2 of the annular space 5, the wings 24a and 24b bear on the wall 6 of said annular space 5, i.e. on the external wall 6 of the internal duct 4, so as to exert a pressing force directed at the wall 2 and press the sensors 11 flat against said wall 2.

To carry out the test on the external wall 6 of the annular space 5, the wings 24a and 24b bear on the wall 2 of said space 5, i.e. on the internal wall 2 of the external duct 1, so as to exert a pressing force directed at the wall 6 and press the sensors 11 flat against said wall 6.

The shell 12 is made from a polymer, for example polyurethane, and it may include metallic inserts embedded in the polymer. According to one variant the shell 12 may be made from different, mutually compatible polymers.

The moulding techniques used to produce the shell 12 are of a conventional type, such as for example drop moulding, injection moulding or even dead moulding.

In the course of moving the probe 10 inside the duct 1 in order to inspect the internal wall 2, the resilient portion 14 ensures uniform pressing of the sensor 11, in spite of the distortions and irregularities in the surface of the internal wall 2.

According to one variant, the body 13 or 23 of the shell 12 may feature one or more seats accommodated in said body, for the positioning of various components.

Moreover, the probe 10 may be operatively associated with other probes connected to one another in articulated fashion, for example by a cardan system or else by a "dolly axle" or "shock mount" type system, so as to constitute a set of probes that can be moved along the duct under test.

The design of the probe according to the invention makes possible lower manufacturing costs, simplifies the engineering principles involved when compared to the probes used up till now, and improves the reliability and service life of the inspection probe.

What is claimed is:

1. Probe for inspecting an internal wall of a duct, comprising at least one sensor mounted in a support adapted to be moved along the duct while pressing said sensor flat against the internal wall, wherein the support is formed by a shell molded onto said sensor and featuring, on the one hand, a body provided with at least one window for positioning said sensor and, on the other hand, means for pressing said sensor flat against the internal wall which means are integrally molded with the body.

2. Inspection probe according to claim 1, wherein the duct presents a circular cross-section and the body has a substantially circular cross-section slightly smaller than the section of said duct.

3. Inspection probe according to claim 1, wherein the duct comprises an internal duct which together with said duct accommodates an annular space, and the body has a substantially trapezoidal cross-section of a slightly lesser thickness than the width of said space.

4. Inspection probe according to claim 1, wherein the pressing means include at least one portion of the body that is resilient and projects with respect to said body, designed to bear against the internal wall of the duct or against an internal wall of the annular space, so as to exert a force in the direction of the window and press the sensor flat against said internal wall.

5. Inspection probe according to claim 4, wherein the pressing force exerted by said resilient portion on the sensor is between 2 and 25 newtons, preferably between 5 and 15 newtons.

6. Inspection probe according to claim 4, wherein said resilient portion extends over at least part of the length of the body of the shell.

7. Inspection probe according to claim 4, wherein said resilient portion extends the full length of the body of the shell.

8. Inspection probe according to claim 4, wherein said resilient portion is located on the body, opposite to the contact generator for the sensor with respect to the internal wall.

9. Inspection probe according to claim 8, wherein said resilient portion is formed by two non-rigid pressing wings.

10. Inspection probe according to claim 9, wherein the pressing wings are arranged 120° to either side of the contact generator for the sensor with respect to the internal wall.

11. Inspection probe according to claim 4, wherein said resilient portion is located on the lateral edges of the body.

12. Inspection probe according to claim 11, wherein said resilient portion is formed by two non-rigid pressing wings.

13. Inspection probe according to claim 12, wherein the pressing wings are arranged 120° to either side of the contact generator for the sensor with respect to the internal wall.

14. Inspection probe according to claim 1, wherein the shell is produced from at least one polymer, for example polyurethane.

15. Inspection probe according to claim 14, wherein the shell incorporates inserts, for example made of metal.

16. Inspection probe according to claim 1, wherein the sensor is an ultrasonic sensor.

17. Inspection probe set, wherein it features multiple inter-articulated probes according to claim 1.

* * * * *